US011077181B2

(12) United States Patent
Sno et al.

(10) Patent No.: US 11,077,181 B2
(45) Date of Patent: Aug. 3, 2021

(54) VACCINE COMPRISING A PCV2 ORF2 PROTEIN OF GENOTYPE 2B

(71) Applicant: Intervet Inc., Madison, NJ (US)

(72) Inventors: Melanie Sno, Budapest (HU); Erik Cox, Nijmegen (NL); Ruud Philip Antoon Maria Segers, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/634,756

(22) PCT Filed: Aug. 2, 2018

(86) PCT No.: PCT/EP2018/070955
§ 371 (c)(1),
(2) Date: Jan. 28, 2020

(87) PCT Pub. No.: WO2019/025519
PCT Pub. Date: Feb. 7, 2019

(65) Prior Publication Data
US 2020/0206340 A1 Jul. 2, 2020

(30) Foreign Application Priority Data
Aug. 3, 2017 (EP) .................................... 17184630

(51) Int. Cl.
*A61K 39/12* (2006.01)
*A61K 39/00* (2006.01)
(52) U.S. Cl.
CPC ........ *A61K 39/12* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| 2009/0017064 A1* | 1/2009 | Wu ........................ A61K 39/12 424/205.1 |
| 2015/0056248 A1 | 2/2015 | Hawick et al. |
| 2020/0206340 A1* | 7/2020 | Sno ....................... C07K 14/005 |

FOREIGN PATENT DOCUMENTS

| WO | 2007028823 A1 | 3/2007 |
| WO | 2017068352 A1 | 4/2017 |

OTHER PUBLICATIONS

Li et al. (Archives of Virology. Published online: Oct. 2016; 162: 235-246).*
European Search Report application 17184630.6—dated Oct. 26, 2017, 7 pages.

(Continued)

*Primary Examiner* — Shanon A. Foley
(74) *Attorney, Agent, or Firm* — Michael D. Davis

(57) ABSTRACT

The present invention pertains to a vaccine comprising an ORF2 encoded protein of porcine circo virus 2 (PCV2) and a pharmaceutically acceptable carrier, for use in a method to protect a pig against an infection with porcine circo virus type 2 by administering the vaccine to the pig, wherein the vaccine comprises less than 20 µg per dose of the ORF2 encoded protein, the protein being of a porcine circo virus of genotype 2b.

8 Claims, 2 Drawing Sheets

(56) References Cited

OTHER PUBLICATIONS

Figure 1:
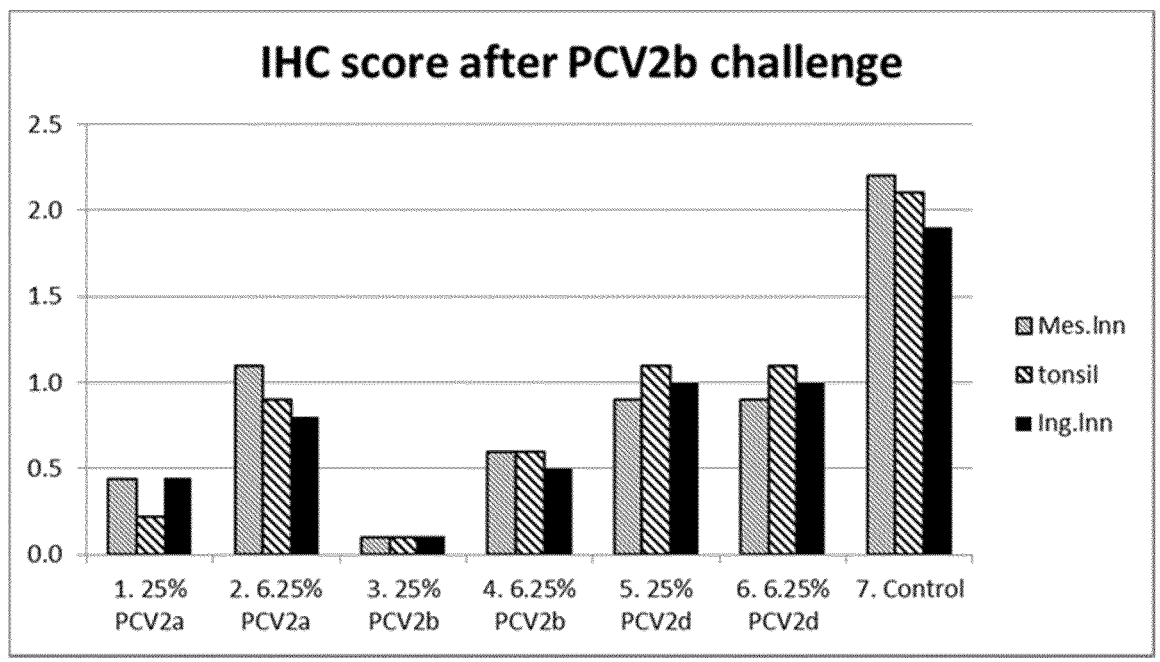

Huang, L et al, Capsid proteins from PCV2a genotype confer greater protection against a PCV2b strain than those from PCV2b genotype in pigs: evidence for PCV2b strains becoming more predominant than PCV2a strains from 2000 to 2010s, Applied Microbiology and Biotechnology, Mar. 28, 2017, 5933-5943, vol. 100, No. 13.
International Search Report for PCT/EP2018/070955, 13 pages.
Karuppannan, A et al, Porcine Circovirus Tyoe 2 (PCV2) Vaccines in the Context of Current Molecular Epidemiology, Viruses, 2017, pp. 1-12, vol. 9.

* cited by examiner

VACCINE COMPRISING A PCV2 ORF2 PROTEIN OF GENOTYPE 2B

CROSS-REFERENCE TO RELATED APPLICATIONS

This application is a national stage entry under 35 U.S.C. § 371 of PCT/EP2018/070955, filed on Aug. 2, 2018, which claims priority to EP Application 17184630.6, filed on Aug. 3, 2017, the content of PCT/EP2018/070955 is hereby incorporated by reference in its entirety.

GENERAL FIELD OF THE INVENTION

The present invention in general pertains to vaccines for protecting pigs against an infection with porcine circo virus type 2.

BACKGROUND OF THE INVENTION

Porcine circovirus type 2 (PCV2) is an economically important swine pathogen and, although small, it has the highest evolution rate among DNA viruses. Since the discovery of PCV2 in the late 1990s, this minimalistic virus with a 1.7 kb single-stranded DNA genome and two indispensable genes (ORF1 and ORF2) has become one of the most important porcine pathogens, and presently is subjected to the highest volume of prophylactic intervention in the form of vaccines in global swine production. The ORF2 gene of PCV encodes the capsid protein of the virus, which at its full length is a protein of about 233 amino acids. The ORF2 gene of all PCV2 isolates share 91-100% nucleotide sequence identity and 90-100% deduced amino acid sequence identity. PCV2 can currently be divided into five different genotypes, PCV2a through PCV2e (Karuppannan and Opriessnig in *Viruses* 2017, 9, 99). It is well documented that PCV2 continues to evolve, which is reflected by changes in the prevalence of genotypes. During 2006, commercial vaccines for PCV2 were introduced on a large scale in a pig population mainly infected with PCV2b. Since 2012, the PCV2d genotype has essentially replaced the previously predominant PCV2b genotype in North America and similar trends are also documented in other geographic regions such as China and South Korea. This is the second major PCV2 genotype shift since the discovery of the virus. The potential increase in virulence of the emergent PCV2 genotype and the efficacy of the current vaccines derived from PCV2a genotype against the PCV2d genotype viruses has received considerable attention.

Vaccines to protect against an infection with PCV2 virus without exception are based on the ORF2 gene of PCV2, comprising either DNA or RNA material for providing a corresponding protein after administration to the subject animal, comprising a protein encoded by the ORF2 gene (e.g. the full length protein, one or more truncated versions or a mixture thereof), or comprising the complete virus and thus inherently, the capsid protein. In the art several vaccines against PCV2 are commercially available. Porcilis® PCV (available from MSD Animal Health, Boxmeer, The Netherlands) is a vaccine for protection of pigs against porcine circo virus type 2, for use in pigs from three weeks and older. When given as a two-shot (two dose) vaccine, the duration of immunity (DOI) is 22 weeks, almost completely covering the fattening period of pigs. Ingelvac CircoFlex® (available from Boehringer Ingelheim, Ingelheim) is a vaccine for protection of pigs against porcine circo virus type 2, for use in pigs from two weeks and older. It is registered as a one-shot (one dose) vaccine only. Circovac® (available from Merial, Lyon, France) is a vaccine for protection of pigs against porcine circo virus type 2, for use in pigs three weeks and older. Suvaxyn® PCV (available from Zoetis, Capelle a/d IJssel, The Netherlands) is a vaccine for protection of pigs against porcine circo virus type 2, for use in pigs from three weeks and older. Other PCV2 vaccines are described for example in WO2007/028823, WO 2007/094893 and WO2008/076915.

The recent review article as mentioned here above (*Viruses* 2017) summarises the current knowledge regarding PCV2 biology, experimental studies on the antigenic variability, molecular epidemiological analysis of the evolution of PCV2 genotypes and PCV2 vaccines. Regarding the latter, it is stated that homologous protection may be better than heterologous protection. Regarding cross protection it is concluded (page 5, lines 29-32) that "controlled experimental studies and field trials show that PCV2a-based vaccines [such as Porcilis PCV and CircoFLEX] and a PCV2b-based vaccine confer adequate cross protection against clinical disease upon challenge with PCV2a, PCV2b and PCV2d genotype viruses and improve average daily weight gain." So it is commonly understood that cross-protection is adequate for each genotye.

OBJECT OF THE INVENTION

It is an object to provide an improved vaccine for protection against an infection with PCV2.

SUMMARY OF THE INVENTION

In order to meet the object of the invention a vaccine comprising an ORF2 encoded protein of porcine circo virus 2 (PCV2) and a pharmaceutically acceptable carrier has been devised, the vaccine being for use in a method to protect a pig against an infection with porcine circo virus type 2 by administering the vaccine to the pig, wherein the vaccine comprises less than 20 µg per dose of the ORF2 encoded protein (e.g. the full length protein, one or more truncated versions or a mixture thereof), the protein being of a porcine circo virus of genotype 2b. The amounts may have any value of 20, 19, 18, 17, 16, 15, 14, 13, 12, 11, 10, 9, 8, 7, 6, 5, 4, 3, 2 or 1 µg per dose.

Surprisingly, against the current knowledge as reflected in *Viruses* 2017, it was found that below a dose of 20 µg of ORF2 encoded protein (from now on also called "ORF2 protein"), the protein derived from PCV2 genotype 2b provides markedly better cross-protection than ORF2 protein of genotype 2a which is present in most commercial vaccines, including the vaccines that dominate the market (i.e. Porcilis PCV of MSD Animal Health and CircoFLEX of Boehringer Ingelheim). Above 20 µg no difference in cross protection is observed. Since Porcilis PCV and CircoFLEX both contain levels well above 20 µg per dose, this explains why both vaccines are successful in protection against heterologous challenge. However, using ORF2 protein of PCV2b provides the opportunity to lower the amount of antigen in the vaccine and still arrive at an adequate cross-protection. This is not only helpful from an economic point of view, but may become very relevant for avoiding interference between antigens in ready-to-use combination vaccines, or for vaccination strategies using less vaccine volume such as intradermal vaccination.

The minimum amount of the ORF2 encoded protein per dose is the amount at which protective immunity against an infection with PCV2 can still be obtained. This can be established by routine experimentation and depends i.a. on the required level of protection. For the current vaccine, based on present data and prior art regarding the minimum protective amount of an ORF2 protein in a vaccine (see i.a. WO2006/072065) a minimum amount is believed to be 0.2 μg of the antigen per dosis, but it may be any higher dosis such as 0.3, 0.4, 0.5, 0.6, 0.7, 0.8, 0.9 and 1.0 μg per dosis.

It is noted that the invention also pertains to the vaccine as such and to a method of protecting a pig against an infection with porcine circo virus type 2, by administering this vaccine to the pig.

Definitions

A vaccine is a pharmaceutical composition that is safe to administer to a subject animal, and is able to induce protective immunity in that animal against a pathogenic micro-organism, i.e. to induce a successful protection against an infection with the micro-organism.

A pharmaceutically acceptable carrier is a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the corresponding vaccine.

Protection against an infection with a micro-organism is aiding in preventing, ameliorating or curing an infection with that micro-organism or a disorder arising from that infection, for example to prevent or reduce one or more clinical signs associated with the infection with the pathogen.

A vaccine that provides protection after one single administration means that protective immunity is conferred after only one single shot of the vaccine, and thus, that a booster vaccination is not necessary to arrive at the said protective immunity. In a two-shot regime, the first (prime) vaccination is typically boosted within 6 weeks from the first administration, commonly within 3 or even 2 weeks from the first administration, and only after the second (boost) administration protective immunity, i.e. a successful protection as defined here above, is understood to be obtained.

EMBODIMENTS OF THE INVENTION

In a first embodiment, the vaccine comprises less than 5 μg per dose. It has been shown that even at an 1/16 dose of the full dose of an 80 μg ORF2 protein containing vaccine adequate cross-protection can be obtained with a PCV2b genotype ORF2 protein.

In a second embodiment the vaccine is for use in pigs having anti-PCV2 antibodies. It was very surprising to establish that protective immunity against PCV2 could be obtained with a dose of the ORF2 protein of genotype 2b below 20p. From the prior art, e.g. EP 1926496, it is known that a dose above 20 μg is needed to arrive at an adequate protection in seropositive piglets with an ORF2 protein of genotype 2a. Indeed, commercial successful PCV2 vaccines like Porcilis PCV and CircoFLEX are administered at a dose well above 20 μg. Thus, the present invention provides the option to use less than 20 μg of the ORF2 protein per dose, even when the anti-PCV2 antibodies are of maternal origin.

In another embodiment the vaccine is for use in pigs having an age of 4 weeks or less. In order to arrive at adequate protection in the most critical period of 5-10 weeks of age, vaccination before an age of 4 weeks has found to be adequate, even though there might be interference of maternal antibodies at this young age.

In yet another embodiment the vaccine provides protection after one single administration of the vaccine. It was surprisingly established that even a single dose of the vaccine containing the ORF2 protein of genotype PCV2b was able to provide adequate cross protection at a very low level of 5 μg per dose, whereas ORF2 protein of genotype PCV2a was less able to provide any protection against heterologous challenge with PCV2 virus.

In still another embodiment the vaccine provides protection against PCV2 of heterologous genotypes (i.e. either PCV2a, PCV2c, PCV2d or PVC2e) at a level corresponding to the protection conferred when the pig would have been vaccinated with an ORF2 encoded protein of PCV2 homologous to the challenge PCV2 virus.

In again another embodiment the vaccine provides protection against PCV2 of genotype 2d at a level corresponding to the protection conferred when the pig would have been vaccinated with an ORF2 encoded protein of PCV2d.

The invention will now be further explained using the following non-limiting examples.

Example 1 describes methods for determining the amount of ORF2 protein in a sample.

Example 2 describes the establishment of cross protection of ORF2 protein of PCV2a, 2b and 2d.

FIG. 1 schematically shows the IHC score after PCV2b challenge.

Figure 2:
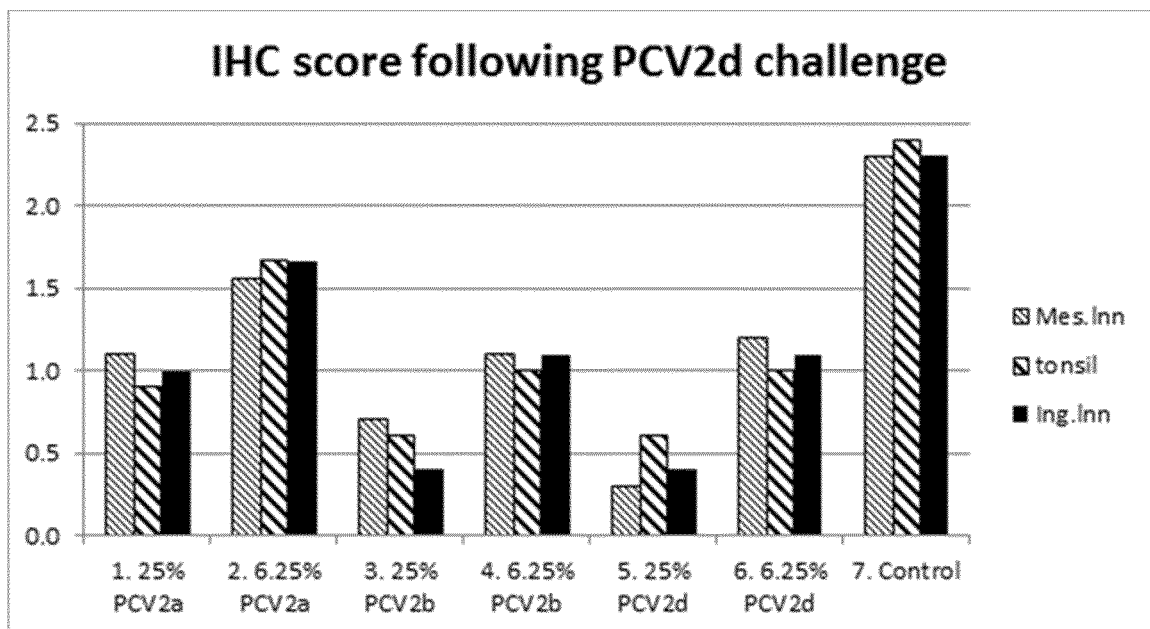

FIG. 2 schematically shows the IHC score after PCV2d challenge.

EXAMPLES

Example 1: Methods for Determining the Amount of ORF2 Protein in a Sample

The amount of ORF2 encoded protein can be determined by any art known method. EP 1926496, in example 4 describes a common method based on SDS-polyacrylamide gel electrophoresis (SDS-PAGE) and coloration with Coomassie Briliant Blue. This type of method for determining the protein content of a sample is commonly known and for example described in The Protein Protocols Handbook, $2^{nd}$ edition, September 2002, edited by J. M. Walker, Humana Press Inc., Totowa, N.J. Chapter 29, pp 237-242. The full length protein has a length of about 26-27 kDa. Common truncated versions have length typically 2-4 kDa lower. If deemed necessary (for example when other proteins of comparable length are also present in the sample), the correct bands with the ORF2 proteins can be identified using anti-ORF2 antibodies that can be visualised using labelled antibodies.

In an alternative method, the amount of ORF2 encoded protein (also capable of detecting full length protein as well as truncated versions thereof), is established via multiple reaction monitoring (MRM) mass spectrometry using purified ORF2 protein as a standard. For this, the protein is firstly digested, for example by using trypsin. Thereafter the peptides are separated, for example by using liquid chromatography, and then the peptides are subjected to mass spectrometry using a signal peptide (in this case "VEFWPCSPITQGDR") for normalising variations in signal. The signal peptide observed is unique to PCV2 ORF2 digested with trypsin. An elaborate description of the method is given in a declaration of Merill Schaeffer, Ph. D, as sent to the European Patent Office as document "D60" on 23 Aug. 2016 by Boehringer Ingelheim Vetmedica GmbH, represented by Hoffmann Eitle, in its opposition against EP 1926496.

Applying these methods to Porcilis PCV and CircoFLEX reveal that in each case the amount of ORF2 encoded protein is well above 20 μg per dose.

Example 2: Establishment of Cross Protection of ORF2 Protein of PCV2a, 2b and 2d As is known from the art, at a 100% level of existing vaccines, the ORF2 protein of PCV2a and other genotypes provides adequate cross protection, all at comparable levels. In the following experiment, vaccines corresponding to Porcilis PCV were used, diluted either 4 times ("25%" version) or 16 times ("6.25%") version when compared to the vaccine at its full ("100%") dose. The vaccine was made in line with the teaching of EP1926496, having a full dose of about 80 μg of ORF2 encoded protein.

The study was performed to evaluate the efficacy of veterinary vaccines with different PCV2 strains (PCV2a, PCV2b and PCV2d) against PCV2b and PCV2d challenge to investigate whether at some low dosis there is a preference for an ORF2 protein of a particular genotype, in particular when assessing cross protection properties.

For this study 2 separate experiments were performed, each experiment involving 70 animals. The 140 animals were derived from 14 sows and were allotted to 14 treatment groups of 10 animals each. The piglets had detectable levels of anti-ORF2 antibodies ranging from low to very high, the average value for all animals being substantially the same for both experiments (about 5.8 at time of vaccination). The piglets were vaccinated intramuscularly with 2 ml when they were approximately three weeks old. In each experiment of 70 animals, groups 1 through 6 were vaccinated with a PCV2 vaccine with different concentrations of ORF2 encoded PCV2 and strains of different genotypes PCV2, as follows:

Experiment 1

Piglets from group 1 were vaccinated with a 25% dose of PCV2a strain (about 20 μg);
Piglets from group 2 were vaccinated with a 6.25% dose of PCV2a strain (about 5 μg);
Piglets from group 3 were vaccinated with a 25% dose of PCV2b strain (about 20 μg);
Piglets from group 4 were vaccinated with a 6.25% dose of PCV2b strain (about 5 μg);
Piglets from group 5 were vaccinated with a 25% dose of PCV2d strain (about 20 μg);
Piglets from group 6 were vaccinated with a 6.25% dose of PCV2d strain (about 5 μg).
Piglets from control group 7 were not vaccinated.

Experiment 2

Piglets from group 1 were vaccinated with a 25% dose of PCV2a strain (about 20 μg);
Piglets from group 2 were vaccinated with a 6.25% dose of PCV2a strain (about 5 μg);
Piglets from group 3 were vaccinated with a 25% dose of PCV2b strain (about 20 μg);
Piglets from group 4 were vaccinated with a 6.25% dose of PCV2b strain (about 5 μg);
Piglets from group 5 were vaccinated with a 25% dose of PCV2d strain (about 20 μg);
Piglets from group 6 were vaccinated with a 6.25% dose of PCV2d strain (about 5 μg).
Piglets from control group 7 were not vaccinated.

Two weeks post vaccination all animals were transported to Intervet International B.V. challenge facilities. At three weeks post vaccination (6 weeks of age) all animals were challenged using 5.0 log 10 TCID50/mL of wild-type PCV2b challenge virus strain (Experiment 1) or a wild type PCV2d strain (Experiment 2) applied intranasally at 3 mL per nostril. Three weeks post challenge, all animals were necropsied and mesenteric lymph node, tonsil and inguinal lymph node were sampled for the detection of PCV2 virus via an immunohistochemistry (IHC) analysis, using a scoring ranging from 0 (no specific positive staining) to 3 (more than 50% of the lymphoid follicles contain cells with positive staining).

The results are indicated in FIGS. 1 and 2. As becomes clear from FIG. 1 homologous protection of a PCV2b vaccine, as expected, is better than heterologous protection. PCV2a seems to provide a slightly better cross protection against PCV2b than PCV2d, although at the lowest dose there is no difference.

Surprisingly, as FIG. 2 shows, the ORF2 encoded protein of PCV2b provides heterologous protection at the low doses tested at a level which is the same as the homologous protection of the ORF2 encoded protein of PCV2d. This is in contrast with the heterologous protection offered by the ORF2 encoded protein of PCV2a which provides less good protection at the low doses tested. So in contrast with common knowledge that ORF2 protein of PCV2a and PCV2b genotypes provides an equal level of cross protection, it appears that below 20 μg, a dosis which is known to be needed in order to effectively break through MDA against PCV2 (see EP 1926496), the ORF2 encoded protein of PCV2b provides significantly better cross protection that the ORF2 encoded protein of PCV2a. Also, despite the presence of MDA's, adequate protection could be arrived at when compared to control at these low dosis levels, in particular when using the ORF2 encoded protein of PCV2b.

The invention claimed is:

1. A method of protecting a pig against an infection with porcine circo virus type 2, comprising administering to the pig a vaccine comprising an ORF2 encoded protein of porcine circo virus 2 (PCV2) and a pharmaceutically acceptable carrier, wherein the vaccine comprises less than 20 μg per dose of the ORF2 encoded protein, wherein the protein is of a porcine circo virus of genotype 2b; and wherein the vaccine provides protection against PCV2 of genotype 2d at a level corresponding to the protection conferred when the pig is vaccinated with an ORF2 encoded protein of PCV2d.

2. The method of claim 1, wherein the vaccine comprises less than 5 μg per dose of the ORF2 encoded protein.

3. The method of claim 1, wherein the vaccine is for protecting pigs that have antibodies against PCV2.

4. The method of claim 3, wherein the antibodies against PCV2 are of maternal origin.

5. The method of claim 1, wherein the pig is 4 weeks old or less.

6. The method of claim 1, wherein the vaccine provides protection after one single administration of the vaccine.

7. The method of claim 4, wherein the vaccine comprises less than 5 µg per dose.

8. The method of claim 4, wherein one single dose of the vaccine is administered to arrive at the protection.

\* \* \* \* \*